United States Patent
Tiongson et al.

(12)

(10) Patent No.: US 6,515,008 B1
(45) Date of Patent: Feb. 4, 2003

(54) FORMULATION

(75) Inventors: Antonio S. Tiongson, Parsipanny, NJ (US); Chungbin Kim, Parsipanny, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/827,786

(22) Filed: Apr. 6, 2001

Related U.S. Application Data

(60) Provisional application No. 60/202,164, filed on May 4, 2000.

(51) Int. Cl.⁷ .................. A61K 9/14; A61K 31/415; A01N 43/50
(52) U.S. Cl. ............... 514/400; 424/489; 514/819; 514/925; 514/926; 514/937
(58) Field of Search .................. 514/400, 819, 514/925, 926, 937; 424/489

(56) References Cited

U.S. PATENT DOCUMENTS

| | | | | |
|---|---|---|---|---|
| 4,996,222 A | * | 2/1991 | Carlin et al. | 514/400 |
| 5,069,910 A | * | 12/1991 | Kovacic et al. | 424/464 |
| 5,976,578 A | * | 11/1999 | Beyerle et al. | 424/686 |

FOREIGN PATENT DOCUMENTS

| | | | |
|---|---|---|---|
| EP | 0 138 540 A2 | * | 4/1985 |
| JP | 01242522 A | * | 9/1989 |
| WO | WO 94/25006 A1 | * | 11/1994 |

* cited by examiner

Primary Examiner—Jose' G. Dees
Assistant Examiner—Marina Lamm
(74) Attorney, Agent, or Firm—Dara L. Dinner; Stephen Venetianer; Charles M. Kinzig

(57) ABSTRACT

The present invention is directed to a novel pharmaceutical composition of polymorph B which has been found to be stable and palatable for long term commercial usage.

17 Claims, No Drawings

FORMULATION

This application claims the benefit of provisional application U.S. Ser. No. 60/202,164, filed May 4, 2000.

FIELD OF THE INVENTION

The present invention is directed to the formulation of $H_2$-receptor antagonists in liquid formulations.

BACKGROUND OF THE INVENTION

Cimetidine is a histamine $H_2$-antagonist which has been described in U.K. Patent Specification 1,397,436. Cimetidine has been shown to be useful in the treatment of duodenal, gastric, recurrent and stomal ulceration, and reflux oesophagitis and in the management of patients who are at high risk from haemorrhage of the upper gastrointestinal tract.

In the case of certain compounds which have bitterness problems and solubility characteristics, the provision of a dosage form which solves theses problems represents a considerable problem.

Many solutions to the problem of taste masking pharmaceutical compositions of cimetidine have been attempted. For example, cimetidine granules have been coated with various compositions such as ethylcellulose and polyvinyl and acrylic polymers. One such proposal is disclosed in U.S. Pat. No. 4,800,087 wherein a polymer mixture coating is employed. The mixture comprises a high temperature film forming copolymer of polymethyacrylic acid ester and acrylic acid ester and a low temperature film forming copolymers consisting of methacrylic acid ester and styrene acrylate. U.S. Pat. No. 4,892,740 discloses pharmaceutical preparations having improved flavouring characteristics obtained by the drug being coated by a polymeric substance which is soluble in gastric juice.

A non-aqueous, chewable composition for oral delivery of unpalatable drugs has also been attempted. In U.S. Pat. No. 5,597,844, Chauhan, Susil, the composition contains the drug intimately dispersed or dissolved in a pharmaceutically acceptable lipid that is solid at room temperatures. The composition also has a matrix that contains a granulating agent for the total composition and a rapid dispersal agent and optionally additives such as buffering agents, flavoring agents, surfactants and the like.

As noted, cimetidine has a pronounced bitter taste. This is not usually a problem when the dosage form employed is a capsule or a tablet designed to be swallowed, thereafter to disintegrate upon reaching the stomach. However, such dosage forms can be impractical when it is desired to administer a large amount of active ingredient, or to co-administer a relatively bulky second active ingredient such as an antacid or alginate. Moreover many individuals have difficulty in swallowing a solid dosage form. Consequently, a liquid dosage form is desirable but must be able to meet the taste and stability requirements necessary for formulation aspects.

It will be appreciated that a major requirement of such a dosage form is that they must be palatable, since an unpalatable formulation increases the risk of a patient neglecting to take a medicament. Such non-compliance with the dosing regimen will in turn delay or prevent the patient's recovery from the condition under treatment.

A further requirement of such a composition is that once the formulation reaches the stomach, the individual particles, in a liquid dosage form such as a suspension, should release the active ingredient rapidly and completely in order to ensure that substantially all of the active ingredient is absorbed; that is to say the formulation should be bioavailable.

As noted, in the case of cimetidine, because of its bitterness, the provision of such dosage forms represents a considerable problem There are four crystalline forms (hereinafter referred to as polymorphs) of the anhydrous base, and three polymorphs of the monohydrate of the base have been characterized. The anhydrous forms have been designated as polymorphs A–D while the hydrated forms have been designated polymorphs M1–M3.

EP-A-257823 describes a stable aqueous suspension of cimetidine wherein at least 90% of the cimetidine is in the polymorphic B form. It is disclosed that the use of polymorph B overcomes the problem of polymorphic interconversion found in the case of polymorph A suspensions of relatively low viscosity which tend to result in lumpy and non homogeneous suspensions.

EPA 0 138 540-A describes suspensions containing cimetidine and the preferred examples are buffered solutions of high viscosity. Because of the high viscosity, such suspensions are not easily poured from a bottle and consequently are usually formulated in sachets.

U.S. Pat. No. 4,996,222, Pharmaceutical formulations, Carlin et al. discloses a stable pharmaceutical composition suitable for oral administration comprising a suspension of an effective histamine H2-antagonist amount of particulate cimetidine in an aqueous phase wherein substantially all of the cimetidine present is of the polymorphic B form. However, this formulation also failed to achieve a stable composition which masked the taste of cimetidine.

Lastly, U.S. Pat. No. 4,786,735 discloses a process for preparing cimetidine polymorph B Graboyes, et al., comprising precipitating cimetidine from an aqueous-alcoholic solution of an acid addition salt.

It is generally recognized that substantially all formulations of cimetidine currently marketed contain polymorph A. Polymorph A can be prepared by recrystallizing cimetidine from a non aqueous organic solvent, particularly isopropanol, as described in GB No. 1,543,238. This process has been shown to be highly reproducible and to result in cimetidine which is easy to filter and has good bulk handling and formulation properties. A method of preparing another polymorph, polymorph D (sometimes referred to as polymorph Z), has also been disclosed in GB No. 2,108,117A.

In contrast to polymorphs A and D, polymorphs B and C are disclosed by Hegedus as being difficult to handle, due at least in part to their thixotropic properties in aqueous suspension which make separation by conventional methods such as filtration and centrifugation very difficult. This has also been the experience of the applicants up until the time of making the present invention There still exists a need in this field for a liquid formulation of cimetidine which is stable, and taste masks the bitter taste of the product for use in a commercial setting.

SUMMARY OF THE INVENTION

The present invention is directed to a stable pharmaceutical composition comprising cimetidine polymorph B, microcrystalline cellulose, carboxymethylcellulose, propylene glycol, and xanthan gum.

DETAILED DESCRIPTION OF THE INVENTION

The present invention is directed to an unexpectently stable and good tasting liquid formulation of an $H_2$ receptor antagonist. While many teaching abound in the art on how to make a tastemasked, or concealed formulation of an $H_2$ receptor antagonist, the resulting liquid formulation have been commercially unacceptable. The formulations have failed on the basis of taste, and or on long-term stability.

For use herein the term histamine $H_2$-antagonists shall mean cimetidine, ranitidine, famotidine, nizatidine, etinidine, lupitidine, nifentidine, niperotidine, roxatidine, sulfotidine, tuvatidine and zaltidine. Preferably the $H_2$ antagonist is cimetidine, famotidine and ranitidine. More preferably it is cimetidine.

It is well known that for stability purposes in a liquid suspension formulation, the polymorph B form of cimetidine is necessary as the Polymorph A form will precipitate out in the formulation. The present invention utilizes the preferred polymorph form, polymorph B.

This invention relates to new pharmaceutical compositions and methods for their preparation, and in particular it relates to suspensions comprising cimetidine.

It is clear that there has been a need for compositions of cimetidine which are liquid based and are palatable. Cimetidine is absorbed almost exclusively in the small intestine and liquid-based compositions offer the possibility that they could be absorbed more quickly and more efficiently than tablet compositions, particularly tablet compositions which have been coated to minimise unpleasant tastes. However, with solutions of cimetidine, the unpleasant bitter taste is a particular problem. Suspensions of cimetidine could in principle offer the advantage of being more palatable but until recently no stable suspension compositions of cimetidine have been described or sold. Some companies have tried to meet the apparent need for such a product by selling cimetidine powder or granules in sachets which can be extemporaneously mixed with water to produce suspension compositions.

There is the difficulty of polymorphism which gives rise to problems of polymorphic transitions and crystal growth. It is generally recognised that cimetidine can exist in at least 5 different polymorphic forms and that these polymorphic forms differ in crystal habit and crystallisation properties, thermodynamic stability, and solubility and rate of dissolution in water. It is generally recognised that the polymorphic form A has been used almost exclusively in compositions. B. Hegedus and S. Gorog, J. Pharmaceutical & Biomedical Analysis, Vol. 3, No. 4, pp.303–313, 1985. It has now been found that the present invention produces a stable formulation of polymorph B in a suspension dosage form.

Aqueous suspensions of cimetidine polymorph A are thermodynamically unstable and it is found that when many such suspensions are prepared having relatively low viscosity, they are likely, when subjected to fluctuating temperatures, to undergo polymorphic transition into the polymorphic B form. This polymorphic transition, forms polymorph B in situ as very long needle-like crystals, which makes the suspensions lumpy and non-homogeneous thereby introducing dosage inaccuracy and giving rise to an unpleasant mouth feel.

It is an object of this invention to provide a suspension of cimetidine which is stable and, in particular, is of relatively low viscosity such that it can be easily poured from bottle and easily administered using a spoon or like device so that various dosages can be exactly and accurately measured. It is also an object of this invention to form a stable composition to which other ingredients such as antacids or alginates can be added.

We have now found that by preparing suspensions from cimetidine polymorph B, the problem of polymorphic transition and the growth in situ of long needle-like crystals can be avoided.

According to the invention, there is provided a stable pharmaceutical composition suitable for oral administration comprising a suspension of particulate cimetidine in an aqueous phase having a pH of about 6.8 to 8.8, preferably around 6 to 7, and a suspending agent, wherein substantially all of the cimetidine present is of the polymorphic B form, and optionally any other pharmaceutical excipients. The relatively high pH provides for a profile which prevents degredation.

Preferably at least 90% and particularly preferably at least 95% of the cimetidine is in the polymorphic B form. It is preferred that substantially no polymorph A is present.

By stable is meant a suspension which is capable of remaining in a pharmaceutically acceptable condition for a prolonged period, for example at least six months, preferably at least a year and most preferably for more than three years. Thus there should not be significant crystal growth, and any sediment formed should be capable of being re-suspended with only mild agitation, i.e. the sediment should not take the form of a "cake" or lumps which cannot readily be re-suspended. Preferably no sediment should form at all.

Examples of suitable suspending agents for use herein include xanthan gum, hydroxypropylmethylcellulose, methylcellulose, carageenan, sodium carboxymethyl cellulose, and sodium carboxymethyl cellulose/ microcrystalline cellulose mixes, particularly sodium carboxymethyl cellulose/microcrystalline cellulose mixtures. Preferred suspending agents are thixotropic suspending agents such as xanthan gum, carageenan and sodium carboxymethyl cellulose/microcrystalline cellulose mixtures and mixtures thereof. More preferred suspending agents are microcrystalline cellulose blends, such as Avicel RC591, Avicel RC581 and Avicel CL611. Avicel is a trademark of FMC Corporation, and RC591, RC581 and CL611 are mixtures of microcrystalline cellulose and sodium carboxymethyl cellulose. Most preferred for use is a combination of predominately, Avicel CL611 and xanthan gums.

Microcrystalline cellulose is defined in the U.S. Pharmacopoeia National Formulary USP XXI (1985), page 1546, as being partially depolymerised cellulose obtained by treating fibrous plant material-derived alpha cellulose with mineral acids. As with the powdered cellulose, it is described as containing 97.0–102.0% of cellulose calculated on the dried basis.

The amount of suspending agent present will vary according to the particular suspending agent used and the presence or absence of other ingredients which have an ability to act as a suspending agent or which contribute significantly to the viscosity of the composition. In general, however, the amount of suspending agent will lie in the range 1–50% w/w relative to the cimetidine powder or granules.

Examples of suitable sweeteners to be used include bulk sweeteners such as sucrose, hydrogenated glucose syrup, the sugar alcohols sorbitol and xylitol, and sweetening agents such as sodium cyclamate, sodium saccharin, asparatame and ammonium glycyrrhizinate. Preferably a mixture is used, more preferably it is a mixture of sucrose and an artifical sweetner such as saccharin.

Particular examples of celluloses are microcrystalline celluloses such as Emcocel™, (supplied by Edward Mendell of New York) and Avicel™ (supplied by FMC Corporation of Philadelphia, Pa.). Particular grades of Avicel™ include Avicel PH 103, Avicel PH 101 and Avicel PH 105. Further examples of celluloses are powdered celluloses such as Elcema™ (supplied by Degussa of Frankfurt).

Additional excipients include, but are not limited to, flavouring agents, colourants, and preservatives, such as parabens.

Formulation Aspects

One formulation for cimetidine suspension (1%) is shown below.

EXAMPLE 1

| Ingredient Name | Amount % w/w |
|---|---|
| Purified Water, USP | 48.926 |
| Cimetidine Polymorph B | 0.815 |
| Microcrystalline Cellulose/Carboxymethylcellulose Sodium, NF (Avivel CL 611) | 1.650 |
| Saccharin Sodium, USP | 0.130 |
| Propylene Glycol, USP | 0.813 |
| Parabens | 0.073 |
| Xanthan Gum, NF | 0.170 |
| FD&C Dye/colorant | 0.0004 |
| Sucrose, NF | 47.200 |
| Flavours and flavour oils | 0.221 |
| TOTAL | 100% |

A suitable dose of Example 1 for use herein is about 20 ml, which provides for 200 mg of cimetidine.

Method of Manufacture

A description of the manufacturing procedure for the production of cimetidine suspension (1%) is given below.

In general batch temperatures of the above example should not exceed 30° C.

A. Saccharin Phase
   (1) Into a suitable Stainless Steel tank, add water.
   (2) Add Saccharin and mix with either a hand paddle or appropriate mixer until the Saccharin is dissolved.

B. Cimetidine Dispersion Phase
   (1) Into a suitable stainless steel tank, add water.
   (2) Place #1 under a 20–50 HP dissolver equipped with a 10" standard blade and begin mixing slowly or until a vortex is formed.
   (3) While mixing slowly, add Cimetidine. Mix until all of the Cimetidine powder is dispersed and fully wet.

C. Avicel Gum (with Cimetidine) Phase
   (1) Add water to a suitable tank equipped with turbine mixer.
   (2) Mix slowly or until a vortex is formed and add the Cimetidine Dispersion Phase from Step B.
   (3) Rinse the Cimetidine Dispersion Phase Tank with Water and add rinse water into the batch.
   (4) While mixing, add and disperse Microcrystalline Cellulose/Carboxymethylcellulose. Increase mixing speed as phase thickens and mix until the gum is dispersed.

D. Paraben-Xanthan Gum Phase
   (1) Into a suitable kettle, add Propylene Glycol.
   (2) Place #1 under a 20–50 HP Dissolver equipped with a 6" standard blade.
   (3) Mix slowly or until a vortex is formed and slowly heat to about 60°–70° C.
   (4) Turn off heat. Add and dissolve parabens. Continue mixing until the parabens are dissolved.
   (5) Allow the Phase to cool to 30° C. or below.
   (6) While mixing, add the Xanthan Gum. Continue mixing at a speed high enough to form a vortex until the Gum is dispersed with no agglomerates present.

E. Primary Compounding Phase
   (1) Add water to a jacketed stainless steel tank equipped with a turbine mixer and begin mixing slowly or until a vortex is formed.
   (2) Add FD&C color previously dissolved in predetermined amount of water.
   (3) Add the Saccharin Phase from Step A and continue mixing until the batch is uniform.
   (4) While mixing, add the Sucrose. Increase mixing speed, if necessary, to maintain the vortex. Continue mixing until the Sucrose is soaking with no lumps present. Check for agglomerates with a strainer.
   (5) Add the Avicel Gum (with Cimetidine) Phase from Step C through a Disperser equipped with Fine Emulsor Screen.
   (6) Rinse Avicel Gum (with Cimetidine) Phase Tank with water and add rinse water to batch.
   (7) Continue mixing at a speed high enough to form a vortex until the batch is uniform. Check for lumps and undissolved sugar with a strainer.
   (8) While mixing, add the Paraben-Xanthan Gum Phase from Step D. Increase the mixing speed, if necessary, to maintain the vortex and continue mixing until the batch is uniform.
   (9) While mixing, add the appropriate oils and flavors and mix until the batch is uniform.
   (10) Transfer the batch through a Disperser equipped with Fine Emulsor Screen to a Holding Tank equipped with a turbine mixer. Mix slowly or until a vortex is formed for a least 10 minutes.
   (11) Determine batch yield.

It has now been found that the bulk product can remain homogenous without mixing for up a significant commercial time, such as near a week. This provides for useful processing and filing of final products not hereto found.

The present invention has been shown to be unexpectently stable, commerically feasible for processing, and also remains a palatable product for the consumer.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A process for preparing an aqueous suspension of cimetidine polymorph B
   which process comprises
   a) mixing cimetidine polymorph B granules or powder with a suitable amount of water to form a first aqueous dispersion phase; and b) adding to the dispersion phase a first suspending agent or mixture thereof to form a second dispersion phase; and c) adding to the second dispersion phase propylene glycol, a second suspending agent; and if necessary or desired adding to the mixture flavourants, sweeteners or combinations thereof.

2. The process according to claim 1 wherein the suspending agent is a mixture of microcrystalline cellulose, and carboxymethylcellulose.

3. The process according to claim 1 wherein the aqueous phase of the suspension has a pH of about 6.8 to 8.8.

4. The process according to claim 1 wherein the suspension further comprises a dye.

5. The process according to claim 1 wherein the suspension further comprises one or more preservatives.

6. The process according to claim 1 wherein the suspending agent is present in an amount of 1 to 50% w/w to the cimetidine.

7. The product produced by the process according to claim 1.

8. The process according to claim 1 wherein the first or second suspending agent is xanthan gum, hydroxypropylmethylcellulose, methylcellulose, carageenan, sodium carboxymethyl cellulose, and sodium carboxymethyl cellulose/microcrystalline cellulose mixes, particularly sodium carboxymethyl cellulose/microcrystalline cellulose mixtures, and mixtures thereof.

9. The process according to claim 8 wherein the suspending agent is xanthan gum, carageenan and sodium carboxymethyl cellulose/microcrystalline cellulose mixtures and mixtures thereof.

10. The process according to claim 8 wherein the first suspending agent is a microcrystalline cellulose blend, or a mixture of microcrystalline cellulose and sodium carboxymethyl cellulose.

11. The process according to claim 8 wherein the second suspending agent is xanthan gum.

12. The process according to claim 1 wherein the first suspending agent is a mixture of microcrystalline cellulose, and sodium carboxymethyl cellulose and the second suspending agent is xanthan gum.

13. The process according to claim 1 wherein the sweetener is a bulk sweetener; a sugar alcohol, sorbitol and xylitol; an artificial sweetener, and ammonium glycyrrhizinate, or a mixture thereof.

14. The process according to claim 13 wherein the bulk sweetener is sucrose, or hydrogenated glucose syrup.

15. The process according to claim 13 wherein the sugar alcohol is sorbitol or xylitol.

16. The process according to claim 13 wherein the artificial sweetener is sodium cyclamate, sodium saccharin, or aspartame.

17. The process according to claim 1 wherein the sweetener is a mixture of sucrose and an artificial sweetener.

* * * * *